(12) United States Patent
Jovcheva et al.

(10) Patent No.: US 10,716,787 B2
(45) Date of Patent: *Jul. 21, 2020

(54) COMBINATIONS

(71) Applicant: ASTEX THERAPEUTICS LTD, Cambridge (GB)

(72) Inventors: Eleonora Jovcheva, Vosselaar (BE); Timothy Pietro Suren Perera, Geel (BE)

(73) Assignee: ASTEX THERAPEUTICS LTD, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/955,149

(22) Filed: Apr. 17, 2018

(65) Prior Publication Data

US 2018/0296558 A1 Oct. 18, 2018

Related U.S. Application Data

(63) Continuation of application No. 15/128,342, filed as application No. PCT/EP2015/056512 on Mar. 26, 2015, now Pat. No. 10,085,982.

(30) Foreign Application Priority Data

Mar. 26, 2014 (EP) .................................. 14161835

(51) Int. Cl.
*A61K 31/4985* (2006.01)
*A61K 31/5025* (2006.01)
*A61K 31/498* (2006.01)
*A61K 45/06* (2006.01)

(52) U.S. Cl.
CPC ........ *A61K 31/4985* (2013.01); *A61K 31/498* (2013.01); *A61K 31/5025* (2013.01); *A61K 45/06* (2013.01)

(58) Field of Classification Search
CPC .............. A61K 31/4995; A61K 31/506; A61K 31/5025; A61K 31/5377
USPC .................................................. 514/249, 250
See application file for complete search history.

(56) References Cited

U.S. PATENT DOCUMENTS

| | | |
|---|---|---|
| 2,940,972 A | 6/1960 | Roch |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,700,823 A | 12/1997 | Hirth et al. |
| 5,882,864 A | 3/1999 | An et al. |
| 6,218,529 B1 | 4/2001 | An et al. |
| 6,271,231 B1 | 8/2001 | Bergstrand et al. |
| 6,331,555 B1 | 12/2001 | Hirth et al. |
| 7,135,311 B1 | 11/2006 | David et al. |
| 7,432,279 B2 | 10/2008 | Green et al. |
| 8,895,601 B2 | 11/2014 | Saxty et al. |
| 9,145,367 B2 | 9/2015 | Tazi et al. |
| 9,221,804 B2 | 12/2015 | Leonard et al. |
| 9,290,478 B2 | 3/2016 | Saxty et al. |
| 9,303,029 B2 | 4/2016 | Woodhead et al. |
| 9,303,030 B2 | 4/2016 | Angibaud et al. |
| 9,309,241 B2 | 4/2016 | Angibaud et al. |
| 9,309,242 B2 | 4/2016 | Berdini et al. |
| 9,439,896 B2 | 9/2016 | Berdini et al. |
| 9,447,098 B2 | 9/2016 | Saxty et al. |
| 9,464,071 B2 | 10/2016 | Saxty et al. |
| 9,493,426 B2 | 11/2016 | Angibaud et al. |
| 9,527,844 B2 | 12/2016 | Angibaud et al. |
| 9,737,544 B2 | 8/2017 | Angibaud et al. |
| 9,757,364 B2 | 9/2017 | Angibaud et al. |
| 9,850,228 B2 | 12/2017 | Saxty et al. |

(Continued)

FOREIGN PATENT DOCUMENTS

| | | |
|---|---|---|
| CA | 2524525 | 12/2004 |
| CA | 2524948 | 12/2004 |

(Continued)

OTHER PUBLICATIONS

Bronte et al., Ther Adv Med Oncol 2016, vol. 8(3) 188-197.*

(Continued)

*Primary Examiner* — Venkataraman Balasubramanian
(74) *Attorney, Agent, or Firm* — Heslin Rothenberg Farley & Mesiti P.C.

(57) ABSTRACT

The invention relates to a combination of a first compound selected from N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and a second compound which is a cMet inhibitor.

The combination is for use in the treatment of a proliferative disorder, in particular for use in the treatment of cancer.

The FGFR inhibitor (N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof) and the cMet inhibitor can be administered simultaneously, separately or sequentially.

The invention further relates to a pharmaceutical composition comprising a pharmaceutically acceptable carrier and a combination according to the invention.

13 Claims, 4 Drawing Sheets

(56) References Cited

U.S. PATENT DOCUMENTS

| | | |
|---|---|---|
| 9,856,236 B2 | 1/2018 | Saxty et al. |
| 9,902,714 B2 | 2/2018 | Vermeulen |
| 10,039,759 B2 | 8/2018 | Berdini et al. |
| 10,045,982 B2 | 8/2018 | Berdini et al. |
| 10,052,320 B2 | 8/2018 | Woodhead et al. |
| 10,085,982 B2 | 10/2018 | Jovcheva et al. |
| 10,272,087 B2 | 4/2019 | Saxty et al. |
| 10,421,747 B2 | 9/2019 | Vermeulen et al. |
| 10,478,494 B2 | 11/2019 | Karkera et al. |
| 10,519,137 B2 | 12/2019 | Saxty et al. |
| 2003/0207886 A1 | 11/2003 | Plücker et al. |
| 2005/0261307 A1 | 11/2005 | Cai et al. |
| 2005/0272728 A1 | 12/2005 | Altenbach et al. |
| 2005/0272736 A1 | 12/2005 | Altenbach et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0118261 A1 | 5/2009 | Aquila et al. |
| 2009/0221591 A1 | 9/2009 | Hartmann et al. |
| 2009/0263397 A1 | 10/2009 | Buck et al. |
| 2010/0228026 A1 | 9/2010 | Yoshida et al. |
| 2010/0234347 A1 | 9/2010 | Dollinger et al. |
| 2011/0123545 A1 | 5/2011 | Marsh et al. |
| 2012/0302572 A1 | 11/2012 | Kan et al. |
| 2013/0072457 A1 | 3/2013 | Saxty et al. |
| 2013/0096021 A1 | 4/2013 | Chinnaiyan et al. |
| 2013/0267525 A1 | 10/2013 | Saxty et al. |
| 2013/0296326 A1 | 11/2013 | Pollock |
| 2014/0037642 A1 | 2/2014 | McCaffery et al. |
| 2014/0288053 A1 | 9/2014 | Berdini et al. |
| 2014/0296236 A1 | 10/2014 | Berdini et al. |
| 2015/0017637 A1 | 1/2015 | Chinnaiyan et al. |
| 2015/0031669 A1 | 1/2015 | Woodhead et al. |
| 2015/0031703 A1 | 1/2015 | Suzuki et al. |
| 2015/0057293 A1 | 2/2015 | Angibaud et al. |
| 2015/0105368 A1 | 4/2015 | Saxty et al. |
| 2015/0191791 A1 | 7/2015 | Shibata |
| 2015/0203589 A1 | 7/2015 | Iavarone et al. |
| 2015/0239883 A1 | 8/2015 | Angibaud et al. |
| 2015/0291589 A1 | 10/2015 | Saxty et al. |
| 2015/0307945 A1 | 10/2015 | Nakanishi et al. |
| 2016/0031856 A1 | 2/2016 | Saxty et al. |
| 2016/0075666 A1 | 3/2016 | Angibaud et al. |
| 2016/0090633 A1 | 3/2016 | Platero et al. |
| 2016/0108034 A1 | 4/2016 | Angibaud et al. |
| 2016/0213677 A1 | 7/2016 | Angibaud et al. |
| 2016/0220564 A1 | 8/2016 | Woodhead et al. |
| 2016/0235744 A1 | 8/2016 | Berdini et al. |
| 2016/0287699 A1 | 10/2016 | Karkera et al. |
| 2016/0311800 A1 | 10/2016 | Saxty et al. |
| 2017/0000781 A1 | 1/2017 | Berdini et al. |
| 2017/0000796 A1 | 1/2017 | Saxty et al. |
| 2017/0100406 A1 | 4/2017 | Jovcheva et al. |
| 2017/0101396 A1 | 4/2017 | Vermeulen et al. |
| 2017/0105978 A1 | 4/2017 | Angibaud et al. |
| 2017/0119763 A1 | 5/2017 | Jovcheva et al. |
| 2018/0021332 A1 | 1/2018 | Broggini |
| 2018/0127397 A1 | 5/2018 | Saxty et al. |
| 2018/0186775 A1 | 7/2018 | Rowbottom et al. |
| 2020/0108141 A1 | 4/2020 | Karkera et al. |
| 2020/0131153 A1 | 4/2020 | Saxty et al. |

FOREIGN PATENT DOCUMENTS

| | | |
|---|---|---|
| CN | 1128496A A | 8/1996 |
| CN | 102036963 A | 4/2011 |
| EP | 0544445 A2 | 6/1993 |
| EP | 1001946 | 5/2000 |
| EP | 1659175 A1 | 5/2006 |
| EP | 1208231 B1 | 1/2007 |
| EP | 1964837 A1 | 9/2008 |
| EP | 1990342 | 11/2008 |
| EP | 2332939 | 6/2011 |
| EP | 2650293 A1 | 10/2013 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 94/26723 A2 | 11/1994 |
| WO | 95/19169 A2 | 7/1995 |
| WO | 98/54156 A1 | 12/1998 |
| WO | 9909845 A1 | 3/1999 |
| WO | 99/17759 A2 | 4/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 03/055491 A1 | 7/2003 |
| WO | 03/086394 A1 | 10/2003 |
| WO | 2004/006355 A2 | 1/2004 |
| WO | 2004/030635 A2 | 4/2004 |
| WO | 2004/043950 A1 | 5/2004 |
| WO | 2004/056822 A1 | 7/2004 |
| WO | 2004065378 A1 | 8/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/012288 A1 | 2/2005 |
| WO | 2005/039587 A1 | 5/2005 |
| WO | 2005/047244 A2 | 5/2005 |
| WO | 2005/054201 A1 | 6/2005 |
| WO | 2005054231 A1 | 6/2005 |
| WO | 2005/061463 A1 | 7/2005 |
| WO | 2006/040052 A1 | 4/2006 |
| WO | 2006040568 A1 | 4/2006 |
| WO | 2006/066361 A1 | 6/2006 |
| WO | 2006084338 A1 | 8/2006 |
| WO | 2006/092430 A1 | 9/2006 |
| WO | 2006124354 A2 | 11/2006 |
| WO | 2007/003419 A1 | 1/2007 |
| WO | 2007/023186 A1 | 3/2007 |
| WO | 2007054556 A1 | 5/2007 |
| WO | 2007/075567 A1 | 7/2007 |
| WO | 2007/125405 A2 | 11/2007 |
| WO | 2007/132227 A1 | 11/2007 |
| WO | 2007140222 A2 | 12/2007 |
| WO | 2008/003702 A2 | 1/2008 |
| WO | 2008/060907 A2 | 5/2008 |
| WO | 2008/076278 A1 | 6/2008 |
| WO | 2008/078091 A1 | 7/2008 |
| WO | 2008/082198 A1 | 7/2008 |
| WO | 2008079988 A2 | 7/2008 |
| WO | 2008080015 A1 | 7/2008 |
| WO | 2008109465 A2 | 9/2008 |
| WO | 2008112408 A1 | 9/2008 |
| WO | 2008/138878 A2 | 11/2008 |
| WO | 2008/141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009020990 A1 | 2/2009 |
| WO | 2009/064835 A1 | 5/2009 |
| WO | 2009/137378 A1 | 11/2009 |
| WO | 2009/141386 A1 | 11/2009 |
| WO | 2010059771 A1 | 5/2010 |
| WO | 2010/084152 A1 | 7/2010 |
| WO | 2010088177 A1 | 8/2010 |
| WO | 2010/129570 A1 | 11/2010 |
| WO | 2011/026579 A1 | 3/2011 |
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |

(56) References Cited

FOREIGN PATENT DOCUMENTS

| | | |
|---|---|---|
| WO | 2012/106556 A2 | 8/2012 |
| WO | 2012/118492 A1 | 9/2012 |
| WO | 2012/148540 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013076186 A1 | 5/2013 |
| WO | 2013087725 A1 | 6/2013 |
| WO | 2013089882 A2 | 6/2013 |
| WO | 2013133351 A1 | 9/2013 |
| WO | 2013173485 A1 | 11/2013 |
| WO | 2013/179033 A1 | 12/2013 |
| WO | 2013/179034 A1 | 12/2013 |
| WO | 2014007369 A1 | 1/2014 |
| WO | 2014018673 A2 | 1/2014 |
| WO | 2014018841 A1 | 1/2014 |
| WO | 2014051022 A1 | 4/2014 |
| WO | 2014071419 A2 | 5/2014 |
| WO | 2014113729 A2 | 7/2014 |
| WO | 2014/174307 A1 | 10/2014 |
| WO | 2014165710 A2 | 10/2014 |
| WO | 2014193229 A2 | 12/2014 |
| WO | 2015017607 A2 | 2/2015 |
| WO | 2015144803 A1 | 10/2015 |
| WO | 2015144804 A1 | 10/2015 |
| WO | 2015144808 A1 | 10/2015 |
| WO | 2016048833 A2 | 3/2016 |
| WO | 2016128411 A1 | 8/2016 |
| WO | 2016134234 A1 | 8/2016 |
| WO | 2016/161239 A1 | 10/2016 |

OTHER PUBLICATIONS

Katoh M. International Journal of Molecular Medicine 38: 3-15, 2016.*
Cecil Textbook of Medicine, edited by Bennet, J.C., and Plum F., 20th edition,vol. 1, 1004-1010, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
International Search Report for PCT/EP2015/056512 dated Jun. 10, 2015.
Extended European Search Report for European Application No. 14161835.5 dated Mar. 12, 2015.
Yan, L., et al. "An efficient synthesis of quinoxaline derivatives from 4-chloro-4-deoxy-α-D-galactose and their cytotoxic activities", *Bioorganic & Medicinal Chemistry Letters*, vol. 17, No. 3, 2006, pp. 609-612.
Thompson, A.M., et al. "Synthesis and Structure—Activity Relationships of 7-Substituted 3-(2,6-Dichlorophenyl)-1,6-napthyridin-2(1H)-ones as Selective Inhibitors of pp60$^{c\text{-}src}$", *Journal of Medicinal Chemistry*, vol. 43, No. 16, 2000, pp. 3134-3147.
Berge, S. M., et al. "Pharmaceutical Salts", *Journal of Pharmaceutical Sciences*, vol. 66, No. 1, 1977, pp. 1-19.
Deady, L.W. "Ring Nitrogen Oxidation of Amino Substituted Nitrogen Heterocycles with m-Chloroperbenzoic Acid", *Synthetic Communications*, vol. 7(8), 1977, pp. 509-514.
Knights, V., et al. "De-regulated FGF receptors as therapeutic targets in cancer", *Pharmacology & Therapeutics*, 2010; vol. 125(1), pp. 105-117.

Korc, M., et al. "The Role of Fibroblast Growth Factors in Tumor Growth", *Current Cancer Drug Targets*, vol. 9(5), 2009, pp. 639-651.
Angerer, L. M., et al. "Demonstration of Tissue-Specific Gene Expression by in Situ Hybridization", *Methods in Enzymology*, vol. 152, 1987, pp. 649-661.
Deprimo, S.E., et al. "Expression profiling of blood samples from an SU5416 Phase III metastatic colorectal cancer clinical trial: a novel strategy for biomarker identification", *BMC Cancer*, vol. 3, 2003; pp. 1-12.
Orre, M., et al., "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.
Zhou, Wenjun et al., "A Structure-Guided Approach to Creating Covalent FGFR Inhibitors", *Chemistry & Biology*, vol. 17, pp. 285-295 (2010).
Avendaño, C., et al., "Drugs That Inhibit Signalling Pathways for Tumor Cell Growth and Proliferation", *Medicinal Chemistry of Anticancer Drugs*, pp. 251-305 (2008).
Garuti, L., et al., Irreversible Protein Kinase Inhibitors, *Current Medicinal Chemistry*, vol. 18, No. 20, Jul. 1, 2011, pp. 2981-2994.
Vippagunta, S.R. et al., "Crystalline Solids", *Advanced Drug Delivery Reviews*, vol. 48, pp. 3-26 (2001).
Jordan, V.C., "Tamoxifen: A Most Unlikely Pioneering Medicine", *Nature Reviews: Drug Discovery*, vol. 2, pp. 205-213 (2003).
Hackam, D.G., et al., "Translation of Research Evidence From Animals to Humans", *JAMA*, vol. 14, pp. 1731-1732 (2006).
"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).
V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).
"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).
Dorwald, F.Z., "Side Reactions in Organic Synthesis: A Guide to Successful Synthesis Design", Weinheim:WILEY-VCH Verlag GmbH & Co. KGaA, 2005, ISBN: 3-527-31021.5.
Lima, L.M., et al., "Bioisosterism: A Useful Strategy for Molecular Modification and Drug Design", *Current Medical Chemistry*, vol. 12(1), pp. 23-49 (2005).
Patani, G.A., et al., "Bioisosterism: A Rational Approach in Drug Design", *Chem. Rev.* vol. 96, pp. 3147-3176 (1996).
Dieci, M.V., et al., Fibroblast Growth Factor Receptor Inhibitors as a Cancer Treatment: From a Biologic Rationale to Medical Perspectives, *Cancer Discovery*, vol. 3, No. 3, pp. 264-279 (Feb. 2013).
Gallick, G.E., et al., Small-molecule protein tyrosine kinase inhibitors for the treatment of metastatic prostate cancer, *Future Medicinal Chemistry*, vol. 4, No. 1, pp. 107-119 (Jan. 2012).
Study to Assess the Relative Bioavailability of Orally Administered JNJ-42756493 Tablet Versus JNJ-42756493 Capsule in Healthy Participants, ClinicalTrials.gov, pp. 1-4 (2014).
Matsuda, Y., et al., Fibroblast Growth Factor Receptor-2 IIIc as a Novel Molecular Target in Colorectal Cancer, *Current Colorectal Cancer Reports*, vol. 10, No. 1, pp. 20-26 (2014).
Carneiro, B.A., et al., Emerging therapeutic targets in bladder cancer, *Cancer Treatment Reviews*, vol. 41, No. 2, pp. 170-178 (2015).
Fujita, M., et al., Generation of Formaldehyde by Pharmaceutical Excipients and Its Absorption by Meglumine, *Chem. Pharm. Bull*, vol. 57, No. 10, pp. 1096-1099 (2009).
Adcock, J., et al., Diversity oriented synthesis: substitution at C5 in unreactive pyrimidines by Claisen rearrangement and reactivity in nucleophilic substitution at C2 and C4 in pteridines and pyrido [2,3-d]pyrimidines, *Tetrahedron*, vol. 67, pp. 3226-3237 (2011).
Database Caplus, Grina, et al., Preparation of oxohydroquinazolinylaminophenylpropanesulfonamide derivatives

(56) References Cited

OTHER PUBLICATIONS and analogs for use as Raf inhibitors, Document No. 157:465574, Accession No. 2012:1301209 (2012).
Liang, G., et al., "Small molecule inhibition of fibroblast growth factor receptors in cancer", *Cytokine & Growth Factor Reviews*, vol. 24, pp. 467-475 (2013).
Golub, T.R., et al., "Molecular Classification of Cancer: Class Discovery and Class Prediction by Gene Expression Monitoring", *Science*, vol. 286, pp. 531-537 (1999).
Greulich, H., et al., "Targeting mutant fibroblast growth factor receptors in cancer", *Trends in Molecular Medicine*, vol. 17, No. 5, pp. 283-292 (2011).
Freshney, R.I., "Culture of Animal Cells, A Manual of Basic Technique", Published by Alan R. Liss, Inc, New York, pp. 1-6 (1983).
Cohen, P., "The development and therapeutic potential of protein kinase inhibitors", *Current Opinion in Chemical Biology*, vol. 3, pp. 459-465 (1999).
Cecil Textbook of Medicine, edited by Bennet, J.C., and Plum, F., 20th edition, vol. 1, pp. 1004-1010 (1996).
Hynes, N.E., et al., "Potential for Targeting the Fibroblast Growth Factor Receptors in Breast Cancer", *Cancer Research*, vol. 70, pp. 5199-5202 (2010).
Neidle, S., "Cancer Drug Design and Discovery", Elsevier/Academic Press, pp. 427-431 (2008).
Dermer, G.B., "Another Anniversary for the War on Cancer", *Biotechnology*, vol. 12, p. 320 (1994).
Katoh, Y., et al., "FGFR2-related pathogenesis and FGFR2-targeted therapeutics (Review)", *International Journal of Molecular Medicine*, vol. 23, pp. 307-311 (2009).
Jain, V.K., et al., "Challenges and opportunities in the targeting of fibroblast growth factor receptors in breast cancer", *Breast Cancer Research*, vol. 14, No. 208, pp. 1-9 (2012).
Ho, H.K., et al., "Current strategies for inhibiting FGFR activities in clinical applications: opportunities, challenges and toxicological considerations", *Drug Discovery Today*, vol. 19, Issue 1, pp. 51-62 (2014).
Sonpavde, G., et al., "Fibroblast growth factor receptors as therapeutic targets in clear-cell renal cell carcinoma", *Expert Opinion on Investigational Drugs*, vol. 23, Issue 3, pp. 305-315 (2014).
Rodriguez-Vida, A., et al., "Complexity of FGFR signaling in metastatic urothelial cancer", *Journal of Hematology & Oncology*, vol. 8, pp. 119 et seq. (2015).
D.A.Kharkevich, Farmakologiya (Pharmacology), 1996, M., Meditsina, p. 41, chapter 6.A (in Russian Only).
V.G.Belikov, Farmatsevticheskaya khimiya (Pharmaceutical Chemistry), M., Vysshaya shkola, 1993, p. 1, chapter 2.2, pp. 43-47) (in Russian only).
Dienstmann et al., "Genomic Aberrations in the FGFR Pathway: Opportunities for Targeted Therapies in Solid Tumors," Annals of Oncology, vol. 25, Nov. 20, 2013, No. 3, pp. 552-563.
Parker et al., "Emergence of FGFR Family Gene Fusions as Therapeutic Targets in a Wide Spectrum of Solid Tumours," Journal of Pathology, Oct. 29, 2013, vol. 232, No. 1, pp. 4-15.

Arai et al., "Fibroblast Growth Factor Receptor 2 Tyrosine Kinase Fusions Define a Unique Molecular Subtype of Cholangiocarcinoma," Hepatology, Apr. 2014, vol. 59, No. 4, pp. 1427-1434.
Bahleda et al., "Phase 1 Study of JNJ-42756493, a Pan-Fibroblast Growth Factor Receptor (FGFR) Inhibitor, in Patients with Advanced Solid Tumors," Journal of Clinical Oncology, May 2014, vol. 32, No. 15, pp. 2501-2501.
Di Stefano et al., "Detection, Characterization, and Inhibition of FGFR-TACC Fusions in IDH Wild-Type Glioma," Clinical Cancer Research, Jan. 21, 2015, vol. 21, No. 14, pp. 3307-3317.
Parker, B.C., et al., "The tumorigenic FGFR3-TACC3 gene fusion escapes miR-99a regulation in glioblastoma," *The Journal of Clinical Investigation*, 123 (2), pp. 855-865, Feb. 1, 2013.
Bello, et al., "E=3810 is a Potent Dual Inhibitor of VEGFR and FGFR that Exerts Antitumor Activity in Multiple Preclinical Models," vol. 71(4), pp. 1396-1405 (2011).
Database, Geneseq [Online], "FGFR3-TACC3 gene fusion PCR primer, FGFR3-TACC3(F18T11)_qPCR_F SEQ: 15," XP002753027, Database accession No. BAT14432 (2013).
Database, Geneseq [Online], "Human FGFR 2 mRNA target sequence for mdRNA, SEQ ID:3954," XP055257043, Database accession No. ATM46802 (2008).
Gavine, et al., "AZD4547: An Orally Bioavailable, Potent, and Selective Inhibitor of the Fibroblast Growth Factor Receptor Tyrosine Kinase Family," *Cancer Research*, vol. 72(8), pp. 2045-2056 (2012).
International Search Report from PCT/US2015/050996 dated Mar. 23, 2016.
Mengual, et al., BMC Research Notes 1:21, pp. 1-8 (Jun. 2008).
Millholland, et al., Research and Reports in Urology, 4: 33-40 (2012).
Sabnis, et al., "FGFR Fusions in the Driver's Seat," *Cancer Discovery*, vol. 3 (6), pp. 607-609 (2013).
Shinmura, et al., "A novel somatic FGFR3 mutation in primary lung cancer," *Oncology Reports*, vol. 31 (3), pp. 1219-1224 (2014).
Singh, et al., "Transforming Fusions of FGFR and TACC Genes in Human Glioblastoma," *Science*, vol. 337 (6099), pp. 1231-1235 (2012).
Trudel, et al., "Evaluation of XL999, a Potent Inhibitor of FGFR3, for the Potential Treatment of t(4;14) Positive Multiple Myeloma," *Blood*, vol. 110 (11), pp. 741A-742A (2007).
Williams, et al., "Oncogenic FGFR3 gene fusions in bladder cancer," *Human Molecular Genetics*, vol. 22 (4), pp. 795-803 (2013).
Wu, et al., "Identification of Targetable FGFR Gene Fusions in Diverse Cancers," *Cancer Discovery*, vol. 3 (6), pp. 636-647 (2013).
Fujita, Megumi et al., "Stabilization by Meglumine of an Amine Compound Degraded by Formaldehyde in Tablets." International Journal of Pharmaceutics 386.1-2 (2010): 195-200.
Singleton, KR et al., "A Receptor Tyrosine Kinase Network Composed of Fibroblast Growth Factor Receptors, Epidermal Growth Factor Receptor, v-erb-b2 Erythroblastic Leukemia Viral Oncogene Homolog 2, and Hepatocyte Growth Factor Receptor Drives Growth and Survival of Head and Neck Squamous Carcinoma Cell Lines", Molecular Pharmacology, Apr. 2013, vol. 83, No. 4, pp. 882-893.

* cited by examiner

COMBINATIONS

CROSS REFERENCE TO RELATED APPLICATIONS

This application is a continuation of U.S. application Ser. No. 15/128,342, filed with the U.S. Patent and Trademark Office on Sep. 22, 2016, which is a national stage filing under section 371 of International Application No. PCT/EP2015/056512, filed on Mar. 26, 2015, and published on Oct. 1, 2015 as WO 2015/144804, which claims priority to European Application No. 14161835.5, filed on Mar. 26, 2014. The entire contents of WO 2015/144804 are hereby incorporated herein by reference.

FIELD OF THE INVENTION

The invention relates to a combination of a first compound selected from N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and a second compound which is a cMet inhibitor.

The combination is for use in the treatment of a proliferative disorder, in particular for use in the treatment of cancer.

The FGFR inhibitor (N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof) and the cMet inhibitor can be administered simultaneously, separately or sequentially.

The invention further relates to a pharmaceutical composition comprising a pharmaceutically acceptable carrier and a combination according to the invention.

SUMMARY OF THE INVENTION

The present invention relates to a combination of a first compound selected from N-(3,5-dimethoxyphenyl)-N'-(1-methylethyl)-N-[3-(1-methyl-1H-pyrazol-4-yl)quinoxalin-6-yl]ethane-1,2-diamine (compound A) or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound B) or a pharmaceutically acceptable salt thereof or a solvate thereof; and a second compound which is a cMet inhibitor.

BACKGROUND OF THE INVENTION

N-(3,5-dimethoxyphenyl)-N'-(1-methylethyl)-N-[3-(1-methyl-1H-pyrazol-4-yl)quinoxalin-6-yl]ethane-1,2-diamine (compound A) is represented by the following formula

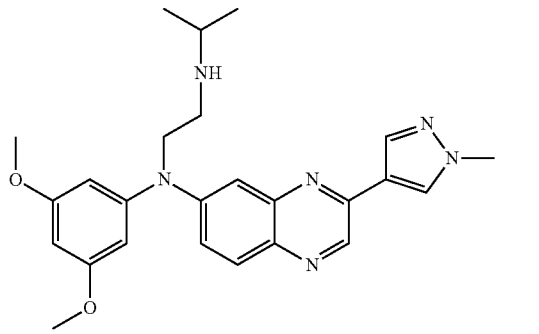

compound A

N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound B) is represented by the following formula

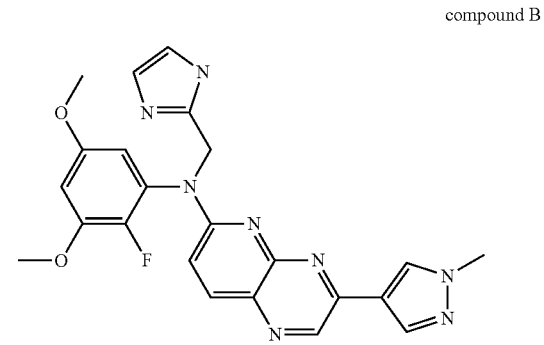

compound B

Compounds N-(3,5-dimethoxyphenyl)-N'-(1-methylethyl)-N-[3-(1-methyl-1H-pyrazol-4-yl)quinoxalin-6-yl]ethane-1,2-diamine (compound A) or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound B) or a pharmaceutically acceptable salt thereof or a solvate thereof, and their chemical synthesis are described in WO2011/135376 and WO2013/061080, which are incorporated herein by reference. They are described as inhibitors or modulators of the activity of certain protein tyrosine kinases, in particular FGFR, and thus the compounds are useful in the treatment or prophylaxis, in particular the treatment, of disease states or conditions mediated by those tyrosine kinases, in particular FGFR. The compounds are useful in the treatment or prophylaxis, in particular the treatment, of cancer.

In WO2011/135376 present compound A is also exemplified as a hydrochloride salt. In WO2013/061080 present compound B is also exemplified as a sulfate salt, as a hydrochloride salt, as a phosphate salt, as a lactate salt, as a fumarate salt.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes. FGFR1 has also been linked to squamous lung cancer, colorectal cancer, glioblastoma, astrocytomas, prostate cancer, small cell lung cancer, melanoma, head and neck cancer, thyroid cancer, uterine cancer.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors. FGFR3 is also linked to endometrial and thyroid cancer.

Over expression of FGFR4 has been linked to poor prognosis in both prostate and thyroid carcinomas. In addition a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated. FGFR4 is also linked to astrocytomas, rhabdomyosarcoma.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs (receptor tyrosine kinases) discussed herein may also find treatment with RTK inhibitors particularly beneficial.

The FGFR kinase inhibitors described herein have a differentiated selectivity profile which provides a new opportunity to use these targeted agents in patient subgroups whose disease is driven by FGFR deregulation. The FGFR kinase inhibitors described herein exhibit reduced inhibitory action on additional kinases, particularly VEGFR, more in particular VEGFR2, and PDGFR, in particular PDGFR-beta, and offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Vascular Endothelial Growth Factor Receptor (VEGFR)

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

cMet

The hepatocyte growth factor (HGF) (also known as scatter factor) receptor, c-Met (Met), is a receptor tyrosine kinase that regulates cell proliferation, morphogenesis, and motility. The c-Met gene is translated into a 170 kD protein that is processed into a cell surface receptor composed of a 140 kD β transmembrane subunit and 50 kD glycosylated extra cellular α subunit.

Mutations in c-Met, over-expression of c-Met and/or HGF/SF (scatter factor), expression of c-Met and HGF/SF by the same cell, and over-expression and/or aberrant c-Met signalling is present in a variety of human solid tumours and is believed to participate in angiogenesis, tumour development, invasion, and metastasis. Cell lines with uncontrolled c-Met activation, for example, are both highly invasive and metastatic. A notable difference between normal and transformed cells expressing c-Met receptor is that phosphorylation of the tyrosine kinase domain in tumour cells is often independent of the presence of ligand.

C-Met mutations/alterations have been identified in a number of human diseases, including tumours and cancers—for instance, hereditary and sporadic human papillary renal carcinomas, breast cancer, colorectal cancer optionally with liver metastases, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelioma, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—and leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma).

Over-expression of c-Met is also believed to be a potentially useful predictor for the prognosis of certain diseases, such as, for example, breast cancer, non-small cell lung carcinoma, pancreatic endocrine neoplasms, prostate cancer, oesophageal adenocarcinoma, colorectal cancer, salivary gland carcinoma, diffuse large B-cell lymphoma and endometrial carcinoma.

Because of the role of aberrant HGF/SF-Met signalling in the pathogenesis of various human cancers, inhibitors of c-Met receptor tyrosine kinase have broad applications in the treatment of cancers in which Met activity contributes to the invasive/metastatic phenotype, including those in which c-Met is not over-expressed or otherwise altered. Inhibitors of c-Met also inhibit angiogenesis and therefore are believed to have utility in the treatment of diseases associated with the formation of new vasculature, such as rheumatoid arthritis and retinopathy.

WO2007/075567 and WO2008/155378, which are incorporated herein by reference, describe cMet inhibitors, such as 6-{difluoro[6-(1-methyl-1H-pyrazol-4-yl)[1,2,4]triazolo[4,3-b]pyridazin-3-yl]methyl}quinoline or a pharmaceutically acceptable salt thereof or a solvate thereof, and 6-[difluoro(6-pyridin-4-yl[1,2,4]triazolo[4,3-b]pyridazin-3-yl)methyl]quinoline or a pharmaceutically acceptable salt thereof or a solvate thereof, and their chemical synthesis, and polymorphs thereof. They are described as protein tyrosine kinase modulators, particularly inhibitors of c-Met, and the use of such compounds to reduce or inhibit kinase activity of c-Met in a cell or a subject, and modulate c-Met expression in a cell or subject, and the use of such compounds for preventing or treating in a subject a cell proliferative disorder and/or disorders related to c-Met, in particular cancer. 6-{Difluoro[6-(1-methyl-1H-pyrazol-4-yl)[1,2,4]triazolo[4,3-b]pyridazin-3-yl]methyl}quinoline (compound C) is represented by the following structure

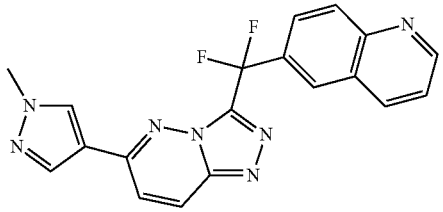

compound C

6-[Difluoro(6-pyridin-4-yl[1,2,4]triazolo[4,3-b]pyridazin-3-yl)methyl]quinoline (compound D) is represented by the following formula

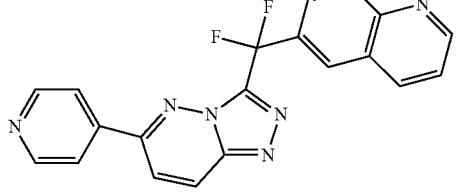

compound D

In WO2008/155378 crystalline forms and hydrates of compound C, in particular Form I, Form II, Form III, and a hydrate form of present compound C are also exemplified.

In WO2008/155378 present compound C is also exemplified as a HBr salt, as a HCl salt, as a methanesulphonate (mesylate) salt, as a ethanesulphonate (esylate) salt and as a p-toluenesulphonate (tosylate).

Compound C or a pharmaceutically acceptable salt thereof or a solvate thereof, and compound D or a pharmaceutically acceptable salt thereof or a solvate thereof, are selective cMet inhibitors.

WO2013/151913 relates to tyrosine kinase inhibitor combinations and their use.

DETAILED DESCRIPTION OF THE INVENTION

Figure 1:
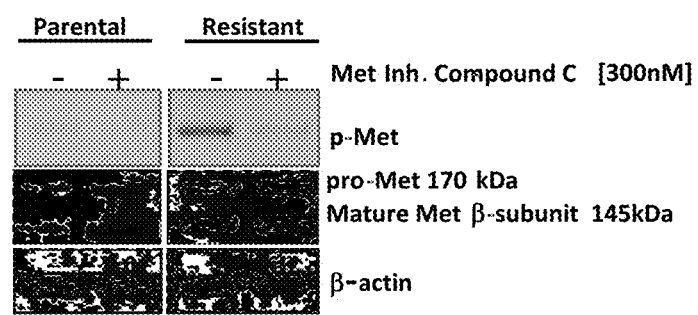
FIG. 1: Western blotting of protein lysates derived from parental and resistant NCI-H1581 cells treated without (−) or with (+) Met inhibitor, 300 nM compound C, for 30 minutes.

The present invention relates to a combination of a first compound selected from N-(3,5-dimethoxyphenyl)-N'-(1-methylethyl)-N-[3-(1-methyl-1H-pyrazol-4-yl)quinoxalin-6-yl]ethane-1,2-diamine (compound A) or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound B) or a pharmaceutically acceptable salt thereof or a solvate thereof, and a second compound which is a cMet inhibitor, in particular a cMet inhibitor as described herein.

In one embodiment, the present invention relates to a combination of N-(3,5-dimethoxyphenyl)-N'-(1-methylethyl)-N-[3-(1-methyl-1H-pyrazol-4-yl)quinoxalin-6-yl]ethane-1,2-diamine (compound A) or a pharmaceutically acceptable salt thereof or a solvate thereof, and a cMet inhibitor, in particular a cMet inhibitor as described herein. In one embodiment, the present invention relates to a combination of N-(3,5-dimethoxyphenyl)-N'-(1-methylethyl)-N-[3-(1-methyl-1H-pyrazol-4-yl)quinoxalin-6-yl]ethane-1,2-diamine (compound A) or a pharmaceutically acceptable salt thereof or a solvate thereof, and 6-{difluoro[6-(1-methyl-1H-pyrazol-4-yl)[1,2,4]triazolo[4,3-b]pyridazin-3-yl]methyl}quinoline or a pharmaceutically acceptable salt thereof or a solvate thereof.

In one embodiment, the present invention relates to a combination of N-(3,5-dimethoxyphenyl)-N'-(1-methylethyl)-N-[3-(1-methyl-1H-pyrazol-4-yl)quinoxalin-6-yl]ethane-1,2-diamine (compound A) or a pharmaceutically acceptable salt thereof or a solvate thereof, and 6-[difluoro(6-pyridin-4-yl[1,2,4]triazolo[4,3-b]pyridazin-3-yl)methyl]quinoline or a pharmaceutically acceptable salt thereof or a solvate thereof. In one embodiment, the present invention relates to a combination of N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound B) or a pharmaceutically acceptable salt thereof or a solvate thereof, and a cMet inhibitor, in particular a cMet inhibitor as described herein.

In one embodiment, the present invention relates to a combination of N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound B) or a pharmaceutically acceptable salt thereof or a solvate thereof, and 6-{difluoro[6-(1-methyl-1H-pyrazol-4-yl)[1,2,4]triazolo[4, 3-b]pyridazin-3-yl]methyl}quinoline or a pharmaceutically acceptable salt thereof or a solvate thereof.

In one embodiment, the present invention relates to a combination of N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound B) or a pharmaceutically acceptable salt thereof or a solvate thereof, and 6-[difluoro(6-pyridin-4-yl[1,2,4]triazolo[4,3-b]pyridazin-3-yl)methyl]quinoline or a pharmaceutically acceptable salt thereof or a solvate thereof.

In one embodiment, the FGFR inhibitor (compound A or a pharmaceutically acceptable salt thereof or a solvate thereof, or compound B or a pharmaceutically acceptable salt thereof or a solvate thereof) and the cMet inhibitor, in particular the cMet inhibitor as described herein, more in particular compound C or a pharmaceutically acceptable salt thereof or a solvate thereof, or compound D or a pharmaceutically acceptable salt thereof or a solvate thereof, of the combinations of the present invention are administered simultaneously (e.g. in separate or unitary compositions) sequentially in either order, at approximately the same time. In this case, the two compounds will be administered in an amount and manner that is sufficient to ensure that an advantageous or synergistic effect is achieved.

In one embodiment, the FGFR inhibitor (compound A or a pharmaceutically acceptable salt thereof or a solvate thereof, or compound B or a pharmaceutically acceptable salt thereof or a solvate thereof) and the cMet inhibitor, in particular the cMet inhibitor as described herein, more in particular compound C or a pharmaceutically acceptable salt thereof or a solvate thereof, or compound D or a pharmaceutically acceptable salt thereof or a solvate thereof, of the combinations of the present invention are administered sequentially in either order, on separate dosing schedules. In this case, the two compounds will be administered within a period and in an amount and manner that is sufficient to ensure that an advantageous or synergistic effect is achieved.

It will be appreciated that the preferred method and order of administration and the respective dosage amounts and regimes for each component of the combination will depend on the particular chemotherapeutic agent being administered, their route of administration, the particular tumor being treated and the particular host being treated.

The optimum method and order of administration and the dosage amounts and regime can be readily determined by those skilled in the art using conventional methods and in view of the information set out herein.

In the combinations of the present invention, the FGFR inhibitor and the cMet inhibitor may be formulated in separate pharmaceutical dosage forms, that can be sold independently from each other, but with the indication or instruction for their combined use. Said indication or instruction can be in the form of a patient leaflet or the like, or in the form of any communication, for instance in written or oral from.

In the combinations of the present invention, the FGFR inhibitor and the cMet inhibitor can be administered via the same route of administration or via different routes of administration.

In one embodiment, the FGFR inhibitor and the cMet inhibitor of the combinations of the present invention are administered via the same route of administration, in particular via oral route.

The present invention also relates to a pharmaceutical product or a commercial package comprising a combination according to the present invention, in particular together with instructions for simultaneous, separate or sequential use in the treatment of an FGFR tyrosine kinase activity mediated disease, especially a cancer.

In one embodiment, in the combinations of the present invention, the FGFR inhibitor and the cMet inhibitor are administered simultaneously.

In one embodiment, in the combinations of the present invention, the FGFR inhibitor and the cMet inhibitor are administered separately, in particular at a time interval that is chosen such that the effect of the combined use is larger than the effect obtained when administering the FGFR inhibitor or cMet inhibitor solely.

In case of a combination of the present invention comprising compound A or a pharmaceutically acceptable salt thereof or a solvate thereof as the FGFR inhibitor it may be advantageous to administer said compound less frequent than the cMet inhibitor because compound A shows lysosomotropic properties and prolonged target shut down.

The FGFR inhibitor and the cMet inhibitor of the combinations of the present invention may also be co-formulated in a single formulation.

In one embodiment, the present invention relates to a pharmaceutical composition comprising a pharmaceutically acceptable carrier and as a first active ingredient a compound selected from N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and as a second active ingredient a cMet inhibitor, in particular a cMet inhibitor as described herein, more in particular a compound selected from 6-{difluoro[6-(1-methyl-1H-pyrazol-4-yl)[1,2,4]triazolo[4,3-b]pyridazin-3-yl]methyl}quinoline or a pharmaceutically acceptable salt thereof or a solvate thereof, and 6-[difluoro(6-pyridin-4-yl[1,2,4]triazolo[4,3-b]pyridazin-3-yl)methyl]quinoline or a pharmaceutically acceptable salt thereof or a solvate thereof.

In one embodiment, the present invention relates to a pharmaceutical composition comprising a pharmaceutically acceptable carrier and as a first active ingredient N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and as a second active ingredient a cMet inhibitor, in particular a cMet inhibitor as described herein.

In one embodiment, the present invention relates to a pharmaceutical composition comprising a pharmaceutically acceptable carrier and as a first active ingredient N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and as a second active ingredient 6-{difluoro[6-(1-methyl-1H-pyrazol-4-yl)[1,2,4]triazolo[4,3-b]pyridazin-3-yl]methyl}quinoline or a pharmaceutically acceptable salt thereof or a solvate thereof.

In one embodiment, the present invention relates to a pharmaceutical composition comprising a pharmaceutically acceptable carrier and as a first active ingredient N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and as a second active ingredient 6-[difluoro(6-pyridin-4-yl[1,2,4]triazolo[4,3-b]-pyridazin-3-yl)methyl]quinoline or a pharmaceutically acceptable salt thereof or a solvate thereof.

In one embodiment, the present invention relates to a pharmaceutical composition comprising a pharmaceutically acceptable carrier and as a first active ingredient N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and as a second active ingredient a cMet inhibitor, in particular a cMet inhibitor as described herein.

In one embodiment, the present invention relates to a pharmaceutical composition comprising a pharmaceutically acceptable carrier and as a first active ingredient N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and as a second active ingredient 6-{difluoro[6-(1-methyl-1H-pyrazol-4-yl)[1,2,4]triazolo[4,3-b]pyridazin-3-yl]methyl}quinoline or a pharmaceutically acceptable salt thereof or a solvate thereof.

In one embodiment, the present invention relates to a pharmaceutical composition comprising a pharmaceutically acceptable carrier and as a first active ingredient N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and as a second active ingredient 6-[difluoro(6-pyridin-4-yl[1,2,4]triazolo[4,3-b]pyridazin-3-yl)methyl]quinoline or a pharmaceutically acceptable salt thereof or a solvate thereof.

In one embodiment, the combinations or pharmaceutical compositions of the present invention are administered orally.

In one embodiment, the combinations or pharmaceutical compositions of the present invention comprise as sole active ingredients a FGFR inhibitor and a cMet inhibitor, including those described in any of the embodiments of the present invention.

In the present invention, in one embodiment, the cMet inhibitor of the combinations or the pharmaceutical compositions of the present invention may also be selected from the group of:
(E)-2-(1-(3-((7-fluoroquinolin-6-yl)methyl)imidazo[1,2-b]pyridazin-6-yl)ethylidene)hydrazinecarboxamide (Example 1 of WO2011/018454); 2-fluoro-N-methyl-4-[(7-quinolin-6-yl-methyl)-imidazo[1,2-b]triazin-2-yl]benzamide (Example 7 of WO 2008/064157); crizotinib; cabozantinib; tivatinib; foretinib; MGCD-265; AMG-208; AMG-337; MK-8033; E-7050; EMD-1204831; EMD-1214063; amuvatinib; BMS-817378; DP-3590; ASP-08001; HM-5016504; PF-4217903; SGX523; antibodies or related molecules, such as for example ficlatuzumab, onartuzumab, rilotuzumab, Tak-701, LA-480;
or a pharmaceutically acceptable salt thereof or a solvate thereof.

In one embodiment, the combinations of the present invention or the pharmaceutical compositions of the present invention comprise at least one further therapeutic agent, in particular at least one further anticancer agent or adjuvant, especially for use as a medicine, more specifically for use in the treatment of cancer or related diseases.

Examples of anti-cancer agents or adjuvants (supporting agents in the therapy) that may be comprised in the combinations or pharmaceutical compositions of the present invention include but are not limited to:
platinum coordination compounds for example cisplatin optionally combined with amifostine, carboplatin or oxaliplatin;
taxane compounds for example paclitaxel, paclitaxel protein bound particles (Abraxane™) or docetaxel;
topoisomerase I inhibitors such as camptothecin compounds for example irinotecan, SN-38, topotecan, topotecan hcl;
topoisomerase II inhibitors such as anti-tumour epipodophyllotoxins or podophyllotoxin derivatives for example etoposide, etoposide phosphate or teniposide;
anti-tumour vinca alkaloids for example vinblastine, vincristine or vinorelbine;
anti-tumour nucleoside derivatives for example 5-fluorouracil, leucovorin, gemcitabine, gemcitabine hcl, capecitabine, cladribine, fludarabine, nelarabine;
alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;
anti-tumour anthracycline derivatives for example daunorubicin, doxorubicin optionally in combination with dexrazoxane, doxil, idarubicin, mitoxantrone, epirubicin, epirubicin hcl, valrubicin;
tetracarcin derivatives for example tetrocarcin A;
glucocorticoiden for example prednisone;
antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
estrogen receptor antagonists or selective estrogen receptor modulators or inhibitors of estrogen synthesis for example tamoxifen, fulvestrant, toremifene, droloxifene, faslodex, raloxifene or letrozole;
aromatase inhibitors such as exemestane, anastrozole, letrazole, testolactone and vorozole;
differentiating agents such as retinoids, vitamin D or retinoic acid and retinoic acid metabolism blocking agents (RAMBA) for example accutane;
DNA methyl transferase inhibitors for example azacytidine or decitabine;
antifolates for example premetrexed disodium;
antibiotics for example antinomycin D, bleomycin, mitomycin C, dactinomycin, carminomycin, daunomycin, levamisole, plicamycin, mithramycin;
antimetabolites for example clofarabine, aminopterin, cytosine arabinoside or methotrexate, azacitidine, cytarabine, floxuridine, pentostatin, thioguanine;
apoptosis inducing agents and antiangiogenic agents such as Bcl-2 inhibitors for example YC 137, BH 312, ABT 737, gossypol, HA 14-1, TW 37 or decanoic acid;
tubuline-binding agents for example combrestatin, colchicines or nocodazole;
kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
farnesyltransferase inhibitors for example tipifarnib;
histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
Inhibitors of the ubiquitin-proteasome pathway for example PS-341, MLN 0.41 or bortezomib;

Yondelis;
Telomerase inhibitors for example telomestatin;
Matrix metalloproteinase inhibitors for example batimastat, marimastat, prinostat or metastat.
Recombinant interleukins for example aldesleukin, denileukin diftitox, interferon alfa 2a, interferon alfa 2b, peginterferon alfa 2b
MAPK inhibitors
Retinoids for example alitretinoin, bexarotene, tretinoin
Arsenic trioxide
Asparaginase
Steroids for example dromostanolone propionate, megestrol acetate, nandrolone (decanoate, phenpropionate), dexamethasone
Gonadotropin releasing hormone agonists or antagonists for example abarelix, goserelin acetate, histrelin acetate, leuprolide acetate
Thalidomide, lenalidomide
Mercaptopurine, mitotane, pamidronate, pegademase, pegaspargase, rasburicase
BH3 mimetics for example ABT-737
MEK inhibitors for example PD98059, AZD6244, CI-1040
colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.
a steroidal cytochrome P450 17alpha-hydroxylase-17,20-lyase inhibitor (CYP17), e.g. abiraterone, abiraterone acetate.

The combinations or pharmaceutical compositions of the present invention also have therapeutic applications in sensitising tumour cells for radiotherapy and chemotherapy.

Hence the combinations or pharmaceutical compositions of the present invention can be used as "radiosensitizer" and/or "chemosensitizer" or can be given in combination with another "radiosensitizer" compound and/or "chemosensitizer" compound.

The term "radiosensitizer" or "radiosensitizer" compound, as used herein, is defined as a combination or pharmaceutical formulation of the present invention, or a molecule, preferably a low molecular weight molecule, that when administered to animals in therapeutically effective amounts increase the sensitivity of the cells to ionizing radiation and/or promote the treatment of diseases which are treatable with ionizing radiation.

The term "chemosensitizer" or "chemosensitizer" compound, as used herein, is defined as a combination or pharmaceutical composition of the present invention, or a molecule, preferably a low molecular weight molecule, that when administered to animals in therapeutically effective amounts increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies The present invention also relates to the use of a combination of the present invention for the manufacture of a medicament for the treatment of a FGFR mediated disorder, in particular cancer.

The present invention also relates to the use of a pharmaceutical composition of the present invention for the manufacture of a medicament for the treatment of a FGFR mediated disorder, in particular cancer.

The present invention also relates to the use of a combination of the present invention for the manufacture of a medicament for the prevention of resistance of a tumour or a cancer to the FGFR inhibitor of the combination or for the delay of resistance of a tumour or a cancer to the FGFR inhibitor of the combination.

The present invention also relates to the use of a pharmaceutical composition of the present invention for the manufacture of a medicament for the prevention of resistance of a tumour or a cancer to the FGFR inhibitor of the pharmaceutical composition or for the delay of resistance of a tumour or a cancer to the FGFR inhibitor of the pharmaceutical composition.

The present invention also relates to the use of a combination of the present invention for the manufacture of a medicament for the prevention of the emergence of resistance of a tumour or a cancer to the FGFR inhibitor of the combination or for the delay of the emergence of resistance of a tumour or a cancer to the FGFR inhibitor of the combination. The present invention also relates to the use of a pharmaceutical composition of the present invention for the manufacture of a medicament for the prevention of the emergence of resistance of a tumour or a cancer to the FGFR inhibitor of the pharmaceutical composition or for the delay of the emergence of resistance of a tumour or a cancer to the FGFR inhibitor of the pharmaceutical composition.

The present invention also relates to the use of a combination of the present invention for the manufacture of a medicament for the prophylaxis or the treatment, in particular for the treatment, of a tumour or a cancer wherein Met signaling pathway activation is a mechanism of resistance of the tumour or the cancer to a FGFR inhibitor.

The present invention also relates to the use of a pharmaceutical composition of the present invention for the manufacture of a medicament for the prophylaxis or the treatment, in particular for the treatment, of a tumour or a cancer wherein Met signaling pathway activation is a mechanism of resistance of the tumour or the cancer to a FGFR inhibitor.

The present invention also relates to the use of a cMet inhibitor, in particular a cMet inhibitor as described herein, more in particular compound C or a pharmaceutically acceptable salt thereof or a solvate thereof, and compound D or a pharmaceutically acceptable salt thereof or a solvate thereof, to prevent resistance, delay resistance, prevent emergence of resistance or delay the emergence of resistance of a tumour or a cancer to a FGFR inhibitor, in particular a FGFR inhibitor as described herein.

The present invention also relates to the use of a combination of the present invention for the manufacture of a medicament for the prophylaxis or the treatment, in particular for the treatment, of a tumour or a cancer mediated by a FGFR kinase and having high Met expression.

The present invention also relates to the use of a pharmaceutical composition of the present invention for the manufacture of a medicament for the prophylaxis or the treatment, in particular for the treatment, of a tumour or a cancer mediated by a FGFR kinase and having high Met expression.

The salt forms of the compounds of the combinations or pharmaceutical compositions of the present invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (+)-DL-lactic), lactobionic, maleic, malic, (−)-L-malic, malonic, (+)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic, then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

In one embodiment, the pharmaceutically acceptable salts of the FGFR inhibitors or the cMet inhibitors of the combinations or the pharmaceutical compositions of the present invention are acid addition salts.

In one embodiment, the combinations or the pharmaceutical compositions of the present invention comprise a salt of compound A, compound B or compound C as described hereinabove in the background of the invention section.

In one embodiment, the combinations or the pharmaceutical compositions of the present invention comprise the FGFR inhibitor in free base form.

In one embodiment, the combinations or the pharmaceutical compositions of the present invention comprise the cMet inhibitor in free base form.

In one embodiment, the combinations or the pharmaceutical compositions of the present invention comprise the FGFR inhibitor and the cMet inhibitor in free base form.

The compounds of the combinations or pharmaceutical compositions of the present invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution. Solvates of the pharmaceutically acceptable salts of the compounds of the combinations or pharmaceutical compositions of the present invention are also encompassed in the term "solvate".

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed by the compounds as described herein are any complexes (e.g. inclusion complexes or clathrates with compounds such as cyclodextrins, or complexes with metals) of the compounds.

Furthermore, the compounds of combinations or pharmaceutical compositions of the present invention may have one or more polymorph (crystalline) or amorphous forms and as such are intended to be included in the scope of the invention.

In one embodiment, the combinations or the pharmaceutical compositions of the present invention comprise a polymorph or solvate of compound C as described hereinabove in the background of the invention section.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the combinations or the pharmaceutical compositions of the present invention may be useful in alleviating or reducing the incidence of cancer.

The FGFR inhibitors of the combinations and pharmaceutical compositions have activity against FGFR1, FGFR2, FGFR3, and/or FGFR4, and in particular against FGFR1, FGFR2, FGFR3 and FGFR4.

As a consequence of their activity in modulating or inhibiting FGFR, the combinations or pharmaceutical compositions of the present invention will be useful in providing a means of preventing the growth or inducing apoptosis of neoplasias, particularly by inhibiting angiogenesis. It is therefore anticipated that the combinations or pharmaceutical compositions of the present invention will prove useful in treating or preventing proliferative disorders such as cancers. In addition, the combinations or pharmaceutical compositions of the present invention could be useful in the treatment of diseases in which there is a disorder of proliferation, apoptosis or differentiation.

Examples of cancers which may be treated (or inhibited) by the combinations or pharmaceutical compositions of the present invention include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

Examples of cancers which may be treated (or inhibited) include, but are not limited to, bladder cancer, urothelial cancer, metastatic urothelial cancer, surgically unresectable urothelial cancer, breast cancer, glioblastoma, lung cancer, non small cell lung cancer, squamous cell lung cancer, adenocarcinoma of the lung, pulmonary adenocarcinoma, small cell lung cancer, ovarian cancer, endometrial cancer, cervical cancer, soft tissue sarcoma, head and neck squamous cell carcinoma, gastric cancer, oesophageal cancer, squamous cell carcinoma of the oesophagus, adenocarcinoma of the oesophagus, cholangiocarcinoma, hepatocellular carcinoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The combinations or pharmaceutical compositions of the present invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the combinations or pharmaceutical compositions of the present invention can be used to treat gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the combinations, pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

A further subset of cancers includes bladder, lung, breast, gastric, hepatocellular, colon, hematological malignancies, ovarian, glioblastoma.

A further subset of cancers includes bladder, lung, breast, gastric and hepatocellular.

The combinations or pharmaceutical compositions of the present invention, having FGFR such as FGFR1 inhibitory activity, may be particularly useful in the treatment or prevention of breast cancer in particular Classic Lobular Carcinomas (CLC).

As the combinations or pharmaceutical compositions of the present invention have FGFR4 activity they will also be useful in the treatment of prostate or pituitary cancers, or they will be useful in the treatment of breast cancer, lung cancer, prostate cancer, liver cancer (HCC) or lung cancer.

In particular the combinations or pharmaceutical compositions of the present invention comprising FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the combinations or pharmaceutical compositions of the present invention are useful in the treatment of multiple myeloma (in particular multiple myeloma with t(4; 14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the combinations or pharmaceutical compositions of the present invention are useful in the treatment of lobular carcinomas such as CLC (Classic lobular carcinoma).

As the combinations or pharmaceutical compositions of the present invention have activity against FGFR3 they will be useful in the treatment of multiple myeloma and bladder cancer.

In particular, the compounds have activity against tumours with FGFR3-TACC3 translocation, in particular bladder or brain tumours with FGFR3-TACC3 translocation.

In particular the combinations or pharmaceutical compositions of the present invention are useful for the treatment of t(4; 14) translocation positive multiple myeloma.

In one embodiment the combinations or pharmaceutical compositions of the present invention may be useful for the treatment of sarcoma. In one embodiment the combinations or pharmaceutical compositions of the present invention may be useful for the treatment of lung cancer, e.g. squamous cell carcinoma.

As the combinations or pharmaceutical compositions of the present invention have activity against FGFR2 they will be useful in the treatment of endometrial, ovarian, gastric, hepatocellular, uterine, cervix and colorectal cancers. FGFR2 is also overexpressed in epithelial ovarian cancer, therefore the combinations or pharmaceutical compositions of the present invention may be specifically useful in treating ovarian cancer such as epithelial ovarian cancer.

In one embodiment, the combinations or pharmaceutical compositions of the present invention may be useful for the treatment of lung cancer, in particular NSCLC (non small cell lung cancer), squamous cell carcinoma, liver cancer, kidney cancer, breast cancer, colon cancer, colorectal cancer, prostate cancer.

Combinations or pharmaceutical compositions of the present invention may also be useful in the treatment of tumours pre-treated with VEGFR2 inhibitor or VEGFR2 antibody (e.g. Avastin).

In particular the combinations or pharmaceutical compositions of the present invention may be useful in the treatment of VEGFR2-resistant tumours. VEGFR2 inhibitors and antibodies are used in the treatment of thyroid and renal cell carcinomas, therefore the combinations or pharmaceutical compositions of the present invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR signalling may be determined by means of a cell growth assay as set out below or by a method as set out in the section headed "Methods of Diagnosis".

The compounds of the invention, and in particular those compounds having FGFR inhibitory activity, may be particularly useful in the treatment or prevention of cancers of a type associated with or characterised by the presence of elevated levels of FGFR, for example the cancers referred to in this context in the introductory section of this application.

The combinations or pharmaceutical compositions of the present invention may be useful for the treatment of the adult population. The combinations or pharmaceutical compositions of the present invention may be useful for the treatment of the pediatric population.

The combinations or pharmaceutical compositions of the present invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions wherein the combinations or pharmaceutical compositions of the present invention may be useful consists of inflammatory diseases, cardiovascular diseases and wound healing.

FGFR are also known to play a role in apoptosis, angiogenesis, proliferation, differentiation and transcription and therefore the compounds, combinations, pharmaceutical compositions of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The combinations or pharmaceutical compositions of the present invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The combinations or pharmaceutical compositions of the present invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds, combinations, pharmaceutical compositions of the inventions may also be useful in the treatment of lung fibrosis in particular in idiopathic pulmonary fibrosis.

The over-expression and activation of FGFR in tumor-associated vasculature has also suggested a role for the combinations or pharmaceutical compositions of the present invention in preventing and disrupting initiation of tumor angiogenesis. In particular the combinations or pharmaceutical compositions of the present invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

In one embodiment, there is provided a combination or pharmaceutical composition as defined herein for use in therapy, for use as a medicine. In a further embodiment, there is provided a combination or pharmaceutical composition as defined herein for use in the prophylaxis or treatment, in particular in the treatment, of a disease state or condition mediated by a FGFR kinase.

Thus, for example, the combinations or pharmaceutical compositions of the present invention may be useful in alleviating or reducing the incidence of cancer. Therefore, in a further embodiment, there is provided a combination or pharmaceutical composition as defined herein for use in the prophylaxis or treatment, in particular the treatment, of cancer. In one embodiment, the combination or pharmaceutical composition as defined herein is for use in the prophylaxis or treatment of FGFR-dependent cancer. In one embodiment, the combination or pharmaceutical composition as defined herein is for use in the prophylaxis or treatment of cancer mediated by FGFR kinases.

Accordingly, the invention provides inter alia:

A method for the prophylaxis or treatment of a disease state or condition mediated by a FGFR kinase, which method comprises administering to a subject in need thereof a combination or pharmaceutical composition as defined herein.

A method for the prophylaxis or treatment of a disease state or condition as described herein, which method comprises administering to a subject in need thereof a combination or pharmaceutical composition as defined herein.

A method for the prophylaxis or treatment of cancer, which method comprises administering to a subject in need thereof a combination or pharmaceutical composition as defined herein.

A method for alleviating or reducing the incidence of a disease state or condition mediated by a FGFR kinase, which method comprises administering to a subject in need thereof a combination or pharmaceutical composition as defined herein.

A method of inhibiting a FGFR kinase, which method comprises contacting the kinase with a kinase-inhibiting combination or pharmaceutical composition as defined herein.

A method of modulating a cellular process (for example cell division) by inhibiting the activity of a FGFR kinase using a combination or pharmaceutical composition as defined herein.

A combination or pharmaceutical composition as defined herein for use as a modulator of a cellular process (for example cell division) by inhibiting the activity of a FGFR kinase.

A combination or pharmaceutical composition as defined herein for use in the prophylaxis or treatment of cancer, in particular the treatment of cancer.

A combination or pharmaceutical composition as defined herein for use as a modulator (e.g. inhibitor) of FGFR.

The use of a combination or pharmaceutical composition as defined herein for the manufacture of a medicament for the prophylaxis or treatment of a disease state or condition mediated by a FGFR kinase.

The use of a combination or pharmaceutical composition as defined herein for the manufacture of a medicament for the prophylaxis or treatment of a disease state or condition as described herein.

The use of a combination or pharmaceutical composition as defined herein for the manufacture of a medicament for the prophylaxis or treatment, in particular the treatment, of cancer.

The use of a combination or pharmaceutical composition as defined herein for the manufacture of a medicament for modulating (e.g. inhibiting) the activity of FGFR.

Use of a combination or pharmaceutical composition as defined herein in the manufacture of a medicament for modulating a cellular process (for example cell division) by inhibiting the activity of a FGFR kinase.

The use of a combination or pharmaceutical composition as defined herein for the manufacture of a medicament for prophylaxis or treatment of a disease or condition characterised by up-regulation of a FGFR kinase (e.g. FGFR1 or FGFR2 or FGFR3 or FGFR4).

The use of a combination or pharmaceutical composition as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a combination or pharmaceutical composition as defined herein for the manufacture of a medicament for the prophylaxis or treatment of cancer in a patient selected from a sub-population possessing a genetic aberrations of FGFR3 kinase.

The use of a combination or pharmaceutical composition as defined herein for the manufacture of a medicament for the prophylaxis or treatment of cancer in a patient who has been diagnosed as forming part of a sub-population possessing a genetic aberrations of FGFR3 kinase, in particular a FGFR3-TACC3 translocation, more in particular a bladder cancer with a FGFR3-TACC3 translocation.

A method for the prophylaxis or treatment of a disease or condition characterised by up-regulation of a FGFR kinase (e.g. FGFR1 or FGFR2 or FGFR3 or FGFR4), the method comprising administering a combination or pharmaceutical composition as defined herein.

A method for alleviating or reducing the incidence of a disease or condition characterised by up-regulation of a FGFR kinase (e.g. FGFR1 or FGFR2 or FGFR3 or FGFR4), the method comprising administering a combination or pharmaceutical composition as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene, in particular a FGFR3-TACC3 translocation, more in particular a bladder cancer with a FGFR3-TACC3 translocation; and (ii) where the patient does possess the said variant, thereafter administering to the patient a combination or pharmaceutical composition as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a combination or pharmaceutical composition as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The compounds, the combinations or the pharmaceutical compositions of the invention would therefore find particular application in relation to cancers which express a mutated molecular target such as FGFR. Diagnosis of tumours with such mutations could be performed using techniques known to a person skilled in the art and as described herein such as RTPCRi and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Methods of Diagnosis

Prior to administration of a combination or pharmaceutical composition as described herein, a patient may be screened to determine whether a disease or condition from which the patient is or may be suffering is one which would be susceptible to treatment with a compound having activity against FGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, or to sensitisation of a pathway to normal FGFR activity, or to upregulation of these growth factor signalling pathways such as growth factor ligand levels or growth factor ligand activity or to upregulation of a biochemical pathway downstream of FGFR activation.

Examples of such abnormalities that result in activation or sensitisation of the FGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T674I of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR. The term diagnosis includes screening. By marker we include genetic markers including, for example, the measurement of DNA composition to identify mutations of FGFR. The term marker also includes markers which are characteristic of up regulation of FGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR may mean that the patient would be particularly suitable for treatment with a FGFR inhibitor. Tumours may preferentially be screened for presence of a FGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, or detection of FGFR variants or mutants could be applicable in the present case.

Abnormal levels of proteins such as FGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR including the isoforms thereof, include the measurement of microvessel density. This can for example be measured using methods described by Orre and Rogers (Int J Cancer (1999), 84(2) 101-8).

Therefore all of these techniques could also be used to identify tumours particularly suitable for treatment with the combinations or pharmaceutical compositions of the invention.

The combinations or pharmaceutical compositions of the invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer.

Therefore in a further aspect the invention includes use of a combination or pharmaceutical composition according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a compound, a combination or a pharmaceutical composition of the invention for use in the prophylaxis or treatment of cancer in a patient selected from a sub-population possessing a variant of the FGFR gene (for example G697C mutation in FGFR3 and Gly388Arg polymorphism in FGFR4).

In view of their useful pharmacological properties, the FGFR inhibitors and cMet inhibitors may be formulated into various pharmaceutical forms for administration purposes.

In one embodiment the pharmaceutical composition (e.g. formulation) comprises at least one FGFR inhibitor, or at least one cMet inhibitor or at least one FGFR inhibitor and one cMet inhibitor of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The combination or pharmaceutical composition of the invention is administered in an amount sufficient to exert its anti-tumour activity.

Those skilled in the art could easily determine the effective amount of the FGFR inhibitor and cMet inhibitor as described herein. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the FGFR inhibitor, the cMet inhibitor or the combination of the FGFR inhibitor and cMet inhibitor as described herein, and, from 1 to 99.95% by weight, more preferably from 30 to 99.9% by weight, even more preferably from 50 to 99.9% by weight of a pharmaceutically acceptable carrier, all percentages being based on the total weight of the composition.

For the treatment of the above conditions, the combinations or pharmaceutical compositions of the invention may be advantageously employed, as indicated above, in combination with one or more other medicinal agents, more particularly, with other anti-cancer agents or adjuvants in cancer therapy.

The present invention therefore also relates to a pharmaceutical composition comprising the one or more other medicinal agent and the combination according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a FGFR inhibitor according to the invention, as second active ingredient a cMet inhibitor, in particular a cMet inhibitor as defined herein, more in particular compound C or a pharmaceutically acceptable salt thereof or a solvate thereof or compound D or a pharmaceutically acceptable salt thereof or a solvate thereof, and as further active ingredient one or more anticancer agent, as a combined preparation for simultaneous, separate or sequential use in the treatment of patients suffering from cancer.

The one or more other medicinal agents and the combination according to the present invention may be administered simultaneously (e.g. in separate or unitary compositions) or sequentially in either order. In the latter case, the three or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compounds of the combinations of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compounds of the combinations according to the present invention and the one or more other anticancer agent(s) when given as a combination may be determined by the person skilled in the art. Said ratio and the exact dosage and frequency of administration depends on the particular compounds of the combinations according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the combinations of the instant invention. A particular weight ratio for each couple of the FGFR inhibitor, the cMet inhibitor and the other anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The compounds of the combinations or pharmaceutical compositions of the present invention can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^{3}$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

EXPERIMENTAL PART

During evaluation of the above described compounds A and B as FGFR inhibitors, when testing the compounds in a cell based proliferation assay (alamar blue assay, see herein below), it was found that even the most sensitive cancer cell lines ($IC_{50}<10$ nM), have subpopulation of cells that are not sensitive to the compounds. This was for instance observed by a plateau in the proliferation curve around ~10% of DMSO control (value observed in the assay for DMSO is taken as 100%, and values observed for the dose treatments with compound are calculated as % of 100% DMSO). For example, when NCI-H1581 cells, a large cell lung cancer cell line with FGFR1 amplification, were treated in the proliferation assay with N-(3,5-dimethoxyphenyl)-N'-(1-methylethyl)-N-[3-(1-methyl-1H-pyrazol-4-yl)quinoxalin-6-yl]ethane-1,2-diamine the curve showed to plateau at ~10% of DMSO control, suggesting there are ~10% of cells that are insensitive to the treatment with the compound.

The insensitive cells were isolated and profiled with the aim to determine the active signaling pathways that act as drivers for their survival and/or proliferation. Therefore, NCI-H1581 cells were plated onto 10 cm Collagen I coated plates and placed in an incubator at 37° C., 5% $CO_2$. The cells were grown in growth medium (see below), for the parental cells with or without DMSO control, or in growth medium supplemented with high dose of compound A (1 microM final concentration of compound A in the medium, compound A was added as a sample diluted from a stock solution in DMSO), for the resistant cells, over a prolonged period of time. During the time of growing out the compound insensitive cells, medium supplemented with compound A [1 microM], was changed twice weekly. In the case of the parental cells with or without DMSO control, when the cells reached the confluence close to 100% they were trypsinized and re-plated back on the plate. In the compound treated plates outgrowth of resistant clones were observed. After about 3 weeks from the initial treatment, cells were taken out of the plate by trypsinization and passaged on new plate for further expanding. Resistant cells, same as the parental cells were passaged twice weekly, but the medium of the resistant cells was always supplemented with compound A [1 microM]. (test 1)

Growth Medium

RPMI-1640 (Gibco, 31870-025) 500 ml; 10% FCS (Hyclone, SV30160.03) 57 ml; 1 mM Sodium Pyruvate (Gibco, 11360) 5.7 ml; 2 mM L-Glutamine (Gibco, 25030) 5.7 ml; 50 µg/ml Gentamicin (Gibco, 15750) 5.7 ml.

The resistant cells were profiled for genes that are differentially expressed compared to the parental cells using microarray technology. Two microarray experiments were done. In the first experiment, parental and resistant cells were profiled in order to define genes and pathways different between the two populations and to understand the pathways that drive the resistance to compound A. In the second microarray experiment, the changes in gene expression over time after treatment with compound A were profiled. For that purpose NCI-H1581 cells were treated with DSMO or 1 microM of compound A or left untreated during the time course of 1 day, 1 week and 2 weeks.

In both microarray analyses, the Met oncogene was identified as being upregulated in a time dependent manner in the resistant cells.

This experiment was also done with compound B and also for compound B the Met oncogene was identified as being upregulated in a time dependent manner in the resistant cells.

The observation that Met gene was upregulated prompted experiments to check whether the Met receptor is upregulated on the protein level and is activated and whether Met driven signaling pathway acts as a driver of the resistance.

Therefore the parental and resistant cells were profiled on phosphoRTK (receptor tyrosine kinase) arrays, and also for Met total protein expression and phosphorylation. The sensitivity of the cells to selected Met inhibitors (compound C and D) in the Alamar blue proliferation assay was also tested. It was found that Met protein expression was upregulated and Met protein was phosphorylated only in the resistant cells, and not in the parental cells, suggesting that the Met signaling pathway is activated in the resistant cells. In addition to this observation, treatment of the resistant cells with a potent and selective Met inhibitor, compound C, down regulated significantly Met phosphorylation. Parental NCI-H1581 cells had very low detectable levels of Met protein, and no signal for Met protein phosphorylation (see FIG. 1). Furthermore, in the alamar blue proliferation assays of the parental and resistant cells treated with Met inhibitors compound C and D, the Met inhibitors strongly inhibited the proliferation of the resistant NCI-H1581 cells, but not of the parental NCI-H1581 cells (see Table below, results of repeated experiments are shown).

|  | $IC_{50}$ (M) |
| --- | --- |
| Parental cells treated with compound D | >1.0E−5 |
| Parental cells + DMSO treated with compound D | >3.0E−5 |
| Resistant cells treated with compound D | 3.41E−7<br>4.44E−7 |
| Parental cells treated with crizotinib | 6.91E−6<br>4.95E−6 |
| Resistant cells treated with crizotinib | 1.98E−7<br>1.65E−7 |
| Parental cells treated with compound C | >3.0E−5 (same for all experiments) |
| Resistant cells treated with compound C | 1.36E−7<br>2.44E−8<br>6.97E−8<br>2.18E−7<br>1.68E−7 |

From these data it can be concluded that the NCI-H1581 cells resistant to the tested FGFR inhibitors have Met receptor activated and are dependent on the Met signaling pathway for their proliferation and survival.

Figure 2:
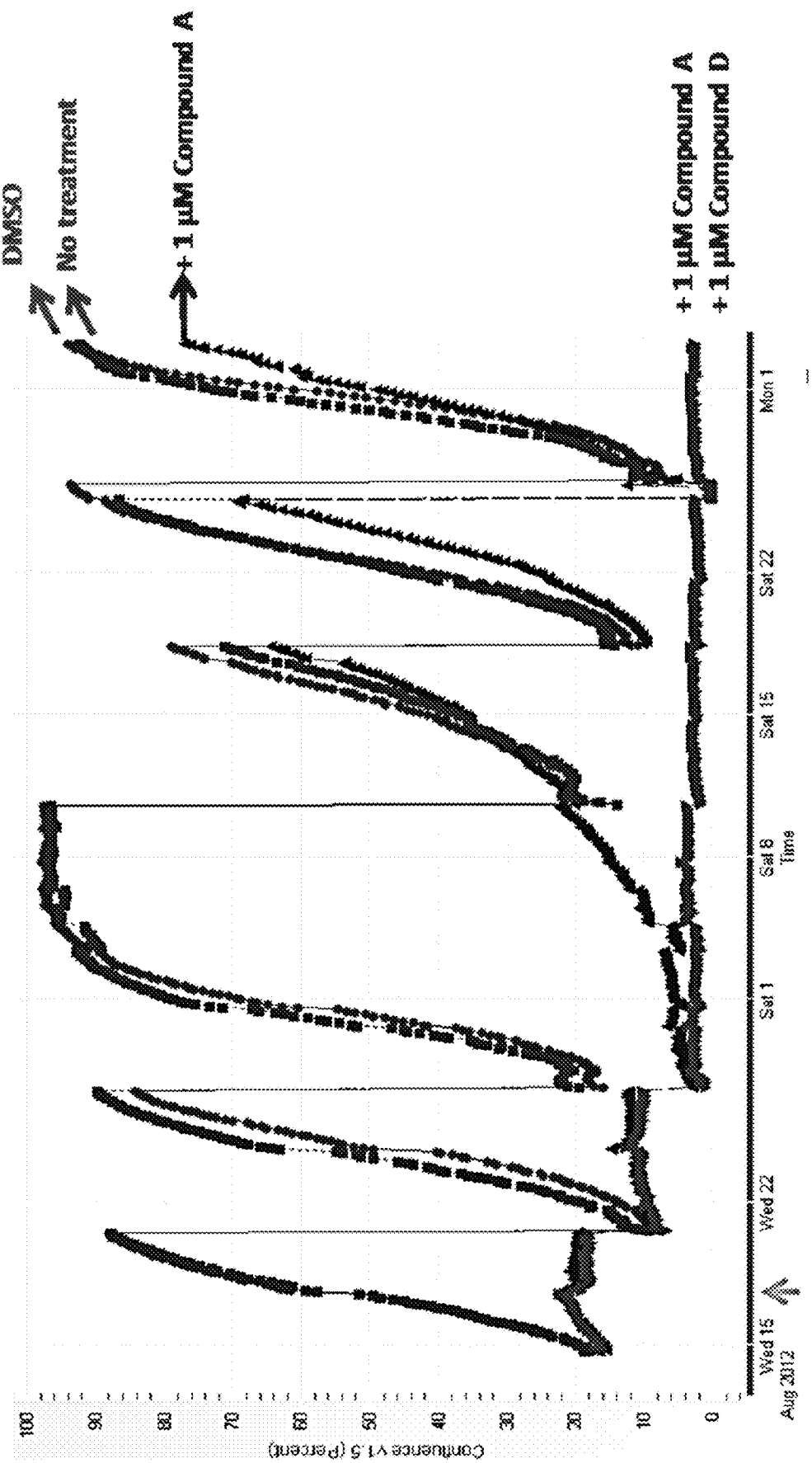
FIG. 2: Incucyte graph (% confluence over time) representing the proliferation of NCI-H1581 cells treated with single agents (compound A [1 microM] or compound D [1 microM]) or combination of both compound A [1 microM] and compound D [1 microM], and DMSO as vehicle control.

The finding of Met signaling activation as a driver of resistance to the tested FGFR inhibitors in NCI-H1581 supports combination treatment with both a FGFR and a Met inhibitor to overcome the emerging of the resistance to a FGFR inhibitor in the NCI-H1581 cells. An experiment was performed where the two agents (FGFR inhibitor: 1 microM compound A, and Met inhibitor: 1 microM compound D) were combined from the beginning. There were also treatments of the cells with single agents (1 microM compound A or 1 microM compound D) or DMSO. The proliferation of the cells was followed using the Incucyt machine, measuring the confluence of the cells over time. In this experiment that was performed in an analogous way as described above for test 1, it was observed that Met inhibitor compound D treatment, as well as DMSO treatment did not impact the proliferation of the NCI-H1581 cells. The treatment of the cells with the FGFR inhibitor (1 microM compound A) initially blocked the proliferation, but after about three weeks emerging outgrowth of compound insensitive cells was observed, which matches with the above indicated finding that after about three week of the continuous inhibition of the FGFR pathway with compound A the insensitive resistant subpopulation of cells in NCI-H1581 cells gained capacity to grow out. Importantly, the combined treatment of FGFR inhibitor (compound A 1 microM) and Met inhibitor (compound D 1 microM) completely prevented emergence of resistance. See FIG. 2.

In Vivo Study

Athymic nude mice were inoculated with resistant NCI-H1581 cells ($10e^6$ cells/200 µl with matrigel, ratio 1:1, into the inguinal region of the mice).

All mice (84) were put into groups (4) and treated from the day of the cell injection.

The mice were treated orally (po), normal volume (250 µl/25 g) once daily and this for 37 days (QD×37). Measurement of the tumor volume was done at day 0, 5, 12, 15, 20, 23, 27, 30, 33, 37.

At day 37 all animals were sacrificed.

The below table illustrates the study design:

| Group | Treatment | Route | Scheme | Animal Number |
|---|---|---|---|---|
| 1 Blanco (10% HP-b-CD) | no | | | 12 |
| 2 Compound A | 25 mg/kg | p.o. | Once daily (QD) for 37 d, after randomization | 24 |
| 3 Compound A Compound D | 25 mg/kg AM 50 mg/kg AM | p.o. | Once daily (QD) for 37 d, after randomization | 24 |
| 4 Compound A Compound D | 25 mg/kg AM 50 mg/kg PM | p.o. | Once daily (QD) for 37 d, after randomization | 24 |

Figure 3:
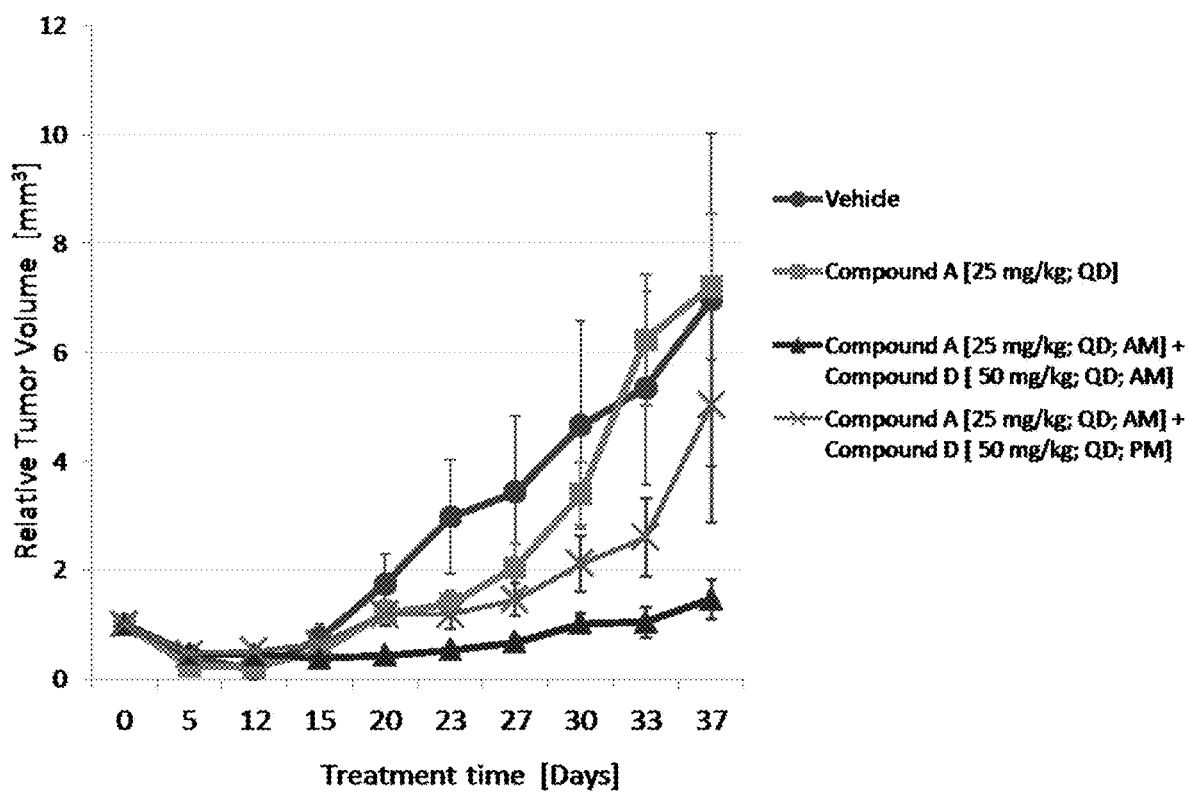
FIG. 3. Efficacy of single agent, compound A, and combination of compound A and compound D in resistant NCI-H1581 xenografts.
Figure 4:
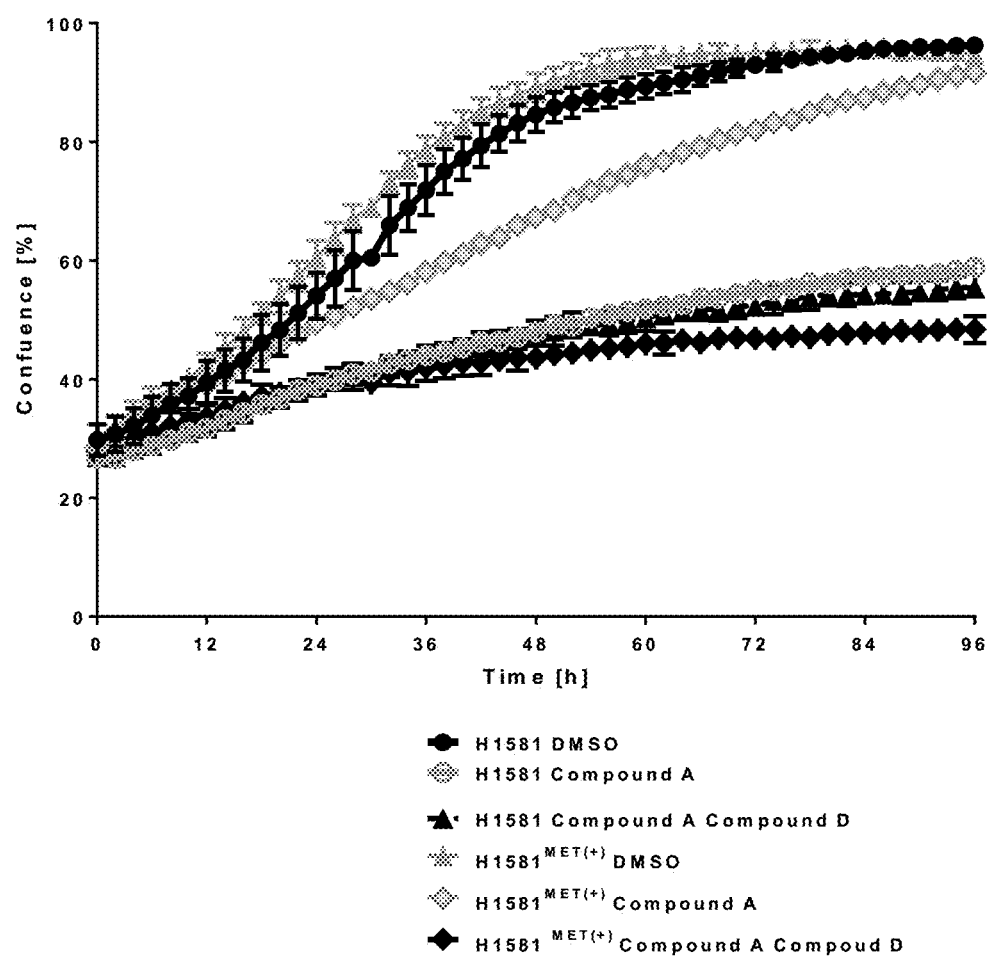
FIG. 4. Incucyte graph (% confluence over time) representing the proliferation of NCI-H1581 cells and NCI-H1581$^{Met(+)}$ cells treated with compound A [0.1 microM] or a combination of compound A [0.1 microM] and compound D [1 microM], and DMSO as vehicle control.

The results of this in vivo study are shown in FIG. 3.

All test agents were tolerated well throughout the study. However, in the combination groups there was observed increased body weight loss.

In this study, it was observed that treatment with compound A did not have effect on tumor growth, since these cells were made prior resistant to this treatment. Interestingly, both combination treatments showed to impact the growth of the tumor. Furthermore, the strongest anti proliferative effect was observed when the two agents were dosed simultaneously. The fact that this model was sensitive to a combination of both targeted agents and insensitive to compound A treatment alone, suggests that both pathways play significant roles in the growth of these tumors.

Alamar Blue Assay

Cells were seeded in 180 µl of medium at optimized cell densities in black 96 well plates with clear flat bottom. The outer wells were filled with 180 µl of medium. Cells were incubated for 24 hours at 37° C. and 5% $CO_2$.

Next day compound dilutions were prepared in a 96 well plate with round bottom (Corning #3365). A 50× dilution of the compound was prepared in medium, 4 µl of compound stock in 196 µl of medium in a 96 well plate (Corning #3585).

Compound/medium plates were placed on a shaker for 10 minutes and then 20 µl of compound in medium was added to the cells (10× dilution). Cells were incubated at 37° C. and 5% $CO_2$ for 4 days until alamarBlue® readout.

Alamarblue® Preparation:
Material:
Resazurin tablets (100 tablets) (PROLABO)
Potassium ferrocyanide (Sigma)
Potassium ferricyanide (Sigma)
$KH_2PO_4$ (Sigma)
$K_2HPO_4$ (Sigma)
Potassium Phosphate Buffer (PPB) 1 Liter
20 mM $KH_2PO_4$ 2.72 g
80 mM $K_2HPO_4$ 13.86 g
pH 7.4 (with a few drops KOH 5M)
Fill to 500 ml with MilliQ
Bring solution to pH 7.4 and adjust to 1 liter of final volume.
PPB-A Reagent
1 Resazurin tablet per ml PPB (1 tablet+800 µl PPB)
PPB-B Reagent 30 mM Potassium Ferri Cyanide in PPB
0.987 g potassium ferri cyanide+100 ml PPB
Filter sterilize over a 0.22 µm filter and store at 4° C.
PPB-C Reagent 30 mM Potassium Ferro Cyanide in PPB
1.266 g potassium ferro cyanide+100 ml PPB
Filter sterilize over a 0.22 µm filter and store at 4° C.
Alamar Blue Mix Ready to Use
1 ml alternative PPB-A+1 ml PPB-B+1 ml PPB-C
add 57 ml PPB
Filter sterilize over a 0.22 µm filter and store at 4° C.

After 4 days of incubation with compound: Add 40 µl of alamarBlue® ready to use mix to each well. Incubate plates at 37° C. and 5% $CO_2$. Measure plates after 4 or 6 hours of incubation (depends on cell line). Shake plates and measure RFU at ex.: 544 nm and em.: 590 nm The alamarBlue® Assay incorporates a fluorometric/colorimetric growth indicator based on detection of metabolic activity. Specifically, the system incorporates an oxidation-reduction (REDOX) indicator that both fluoresces and changes color in response to chemical reduction of growth medium resulting from cell growth.

Inhibition of growth of $H1581^{MET(+)}$ cells by combination of FGFR and MET inhibitors. Parental, unsorted H1581 cells, and sorted $H1581^{Met(+)}$ cells, subpopulation of H1581 cells that have high Met expression, were plated at 75000 cells per well in 24 well plate. One day later, cells were treated with compound A (0.1 mM) or combination of compound A (0.1 mM) and compound D (1 mM), or DMSO serving as a vehicle and the cell proliferation was assessed by measuring cell confluence over a period of four days using Incucyte live cell imaging. Images were acquired every two hours. Proliferation of cells was presented as the mean of percentage of confluence±SD (n=2).

H1581 cells growth was equally inhibited by the treatment with compound A or the combination of compound A and compound D, suggesting that the inhibition of the H1581 cell growth was driven by FGFR inhibitor. $H1581^{MET(+)}$ showed minor sensitivity to compound A, and their proliferation was strongly inhibited by the combination of compound A and compound D, indicating that in this cell population MET kinase is playing significant role in the growth and proliferation. These finding suggest that $H1581^{MET(+)}$ subpopulation is mediating intrinsic resistance to FGFR inhibitors in H1581 cells.

The invention claimed is:

1. A method for the treatment of non small cell lung cancer, which method comprises administering to a subject in need thereof a combination of a first compound selected from N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and a second compound which is a cMet inhibitor, wherein the cMet inhibitor is selected from 6-{difluoro[6-(1-methyl-1H-pyrazol-4-yl)[1,2,4]triazolo[4,3-b]pyridazin-3-yl]methyl}quinoline or a pharmaceutically acceptable salt thereof or a solvate thereof, and 6-[difluoro(6-pyridin-4-yl[1,2,4]triazolo[4,3-b]pyridazin-3-yl)methyl]quinoline or a pharmaceutically acceptable salt thereof or a solvate thereof.

2. The method according to claim 1 wherein the first compound is N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof.

3. The method according to claim 2 wherein the first compound is N-(3,5-dimethoxyphenyl)-N'-(1-methylethyl)-N-[3-(1-methyl-1H-pyrazol-4-yl)quinoxalin-6-yl]ethane-1,2-diamine base.

4. The method according to claim 1 wherein the first compound is N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof.

5. The method according to claim 4 wherein the first compound is N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine base.

6. The method according to claim 1 wherein the cMet inhibitor is 6-{difluoro[6-(1-methyl-1H-pyrazol-4-yl)[1,2,4]triazolo[4,3-b]pyridazin-3-yl]methyl}quinoline or a pharmaceutically acceptable salt thereof or a solvate thereof.

7. The method according to claim 6 wherein the cMet inhibitor is 6-{difluoro[6-(1-methyl-1H-pyrazol-4-yl)[1,2,4]triazolo[4,3-b]pyridazin-3-yl]methyl}quinoline base.

8. The method according to claim 1 wherein the cMet inhibitor is 6-[difluoro(6-pyridin-4-yl[1,2,4]triazolo[4,3-b]pyridazin-3-yl)methyl]quinoline or a pharmaceutically acceptable salt thereof or a solvate thereof.

9. The method according to claim 8 wherein the cMet inhibitor is 6-[difluoro(6-pyridin-4-yl[1,2,4]triazolo[4,3-b]pyridazin-3-yl)methyl]quinolone base.

10. The method according to claim 2 wherein the cMet inhibitor is 6-[difluoro(6-pyridin-4-yl[1,2,4]triazolo[4,3-b]pyridazin-3-yl)methyl]quinoline or a pharmaceutically acceptable salt thereof or a solvate thereof.

11. A method of inhibiting FGFR kinase activity in a cell, which method comprises contacting the cell with a combination of a first compound, wherein the first compound is a FGFR kinase inhibitor selected from N-(3,5-dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and a second compound which is a cMet inhibitor selected from 6-{difluoro[6-(1-methyl-1H-pyrazol-4-yl)[1,2,4]triazolo[4,3-b]pyridazin-3-yl]methyl}quinoline or a pharmaceutically acceptable salt thereof or a solvate thereof, and 6-[difluoro(6-pyridin-4-yl[1,2,4]triazolo[4,3-b]pyridazin-3-yl)methyl]quinoline or a pharmaceutically acceptable salt thereof or a solvate thereof, wherein the second compound delays resistance of the cell to the first compound.

12. The method according to claim 11, comprising inhibiting the FGFR kinase activity of a cell in a subject suffering from, or being at risk of suffering from, a disease state or condition mediated by a FGFR kinase.

13. The method according to claim 12, wherein the subject is a subject suffering from, or being at risk of suffering from cancer.

* * * * *